US012575888B2

(12) United States Patent
Levine et al.

(10) Patent No.: US 12,575,888 B2
(45) Date of Patent: Mar. 17, 2026

(54) PREDICTING STEREOSCOPIC VIDEO WITH CONFIDENCE SHADING FROM A MONOCULAR ENDOSCOPE

(71) Applicant: Covidien LP, Mansfield, MA (US)

(72) Inventors: Steven J. Levine, Framingham, MA (US); Meir Rosenberg, Newton, MA (US); Samuel B. Kesner, Arlington, MA (US)

(73) Assignee: Covidien LP, Mansfield, MA (US)

( * ) Notice: Subject to any disclaimer, the term of this patent is extended or adjusted under 35 U.S.C. 154(b) by 486 days.

(21) Appl. No.: 18/015,603

(22) PCT Filed: Aug. 18, 2021

(86) PCT No.: PCT/US2021/046403
§ 371 (c)(1),
(2) Date: Jan. 11, 2023

(87) PCT Pub. No.: WO2022/040251
PCT Pub. Date: Feb. 24, 2022

(65) Prior Publication Data
US 2023/0248452 A1      Aug. 10, 2023

Related U.S. Application Data

(60) Provisional application No. 63/067,439, filed on Aug. 19, 2020.

(51) Int. Cl.
| | |
|---|---|
| *A61B 34/10* | (2016.01) |
| *A61B 34/30* | (2016.01) |
| *A61B 90/00* | (2016.01) |
| *G06T 5/60* | (2024.01) |
| *G06T 5/77* | (2024.01) |
| *G06T 7/00* | (2017.01) |

(52) U.S. Cl.
CPC .............. *A61B 34/10* (2016.02); *A61B 34/30* (2016.02); *A61B 90/361* (2016.02); *A61B 90/37* (2016.02); *G06T 5/60* (2024.01); *G06T 5/77* (2024.01); *G06T 7/0012* (2013.01); *A61B 2034/301* (2016.02); *A61B 2090/365* (2016.02); *A61B 2090/373* (2016.02); *G06T 2207/10068* (2013.01)

(58) Field of Classification Search
None
See application file for complete search history.

(56) References Cited

U.S. PATENT DOCUMENTS

| | | |
|---|---|---|
| 9,547,940 B1 | 1/2017 | Sun et al. |
| 2012/0086775 A1 | 4/2012 | Bae et al. |
| 2014/0063188 A1 | 3/2014 | Smirnov et al. |

(Continued)

OTHER PUBLICATIONS

International Search Report dated Nov. 26, 2021, issued in corresponding international applicaton No. PCT/US2021/046403, 3 pages.

*Primary Examiner* — Mark R Milia
(74) *Attorney, Agent, or Firm* — Carter, DeLuca & Farrel

(57) ABSTRACT
A surgical robotic system includes an image processing device configured to receive an endoscopic video feed and generate a stereoscopic video feed with confidence shading overlays on display. The confidence shading is based on a level of confidence associated with uncertain regions within images making up the stereoscopic video feed.

20 Claims, 7 Drawing Sheets

(56)  References Cited

U.S. PATENT DOCUMENTS

| | | | |
|---|---|---|---|
| 2015/0248769 | A1 | 9/2015 | Ukil et al. |
| 2019/0053872 | A1 | 2/2019 | Meglan |
| 2020/0297446 | A1* | 9/2020 | Brassett ................. A61B 34/76 |
| 2021/0196109 | A1* | 7/2021 | Shelton, IV ........... A61B 90/30 |

* cited by examiner

801
Render first view of 3D scene based on endoscopic image

803
Render second view of 3D scene based on the endoscopic image

805
Fill-in white areas in the second view

807
Generate stereoscopic image based on the first view and the second view

809
Overlay confidence shading to the stereoscopic image

PREDICTING STEREOSCOPIC VIDEO WITH CONFIDENCE SHADING FROM A MONOCULAR ENDOSCOPE

FIELD

The disclosure is generally related to a robotic surgical system, in particular, to a system and method for predicting stereoscopic video with confidence shading derived from a monocular endoscope during minimally-invasive surgery.

BACKGROUND

Surgical robotic systems are currently being used in minimally invasive medical procedures. Some surgical robotic systems include a surgical console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body.

In minimally-invasive surgery (including robotic-assisted surgery), the surgeon operates surgical instruments, via a robotic surgical system, while viewing a live video feed from an endoscope inserted into the patient. In order for the surgeon to feel immersed in the surgery, it is desirable that he or she be provided with high quality stereoscopic endoscopic video (i.e., separate video channels for each of the surgeon's left and right eye). Without such stereoscopy, estimating depth can be challenging and the surgeon's ability to perform fine manipulation and delicate surgical procedures may be impaired. In addition to this loss of surgical precision, the surgeon may also experience fatigue.

However, in certain surgical settings, stereoscopic endoscopes may not be feasible. Certain surgeries require small endoscopes. Since endoscopes with two optical channels tend to be physically larger (both due to their complexity and due to the need to physically separate the optical paths), they may not be practical for all types of surgeries. Similarly, with endoluminal endoscopy, the technology needed to fluoresce tissue takes up significant space in the endoscope and similarly makes adding a second optical path impractical.

SUMMARY

According to an aspect of the disclosure, algorithms are used that predict stereoscopic video from monocular endoscopes, for the purpose of displaying that information to the surgeon live. With such algorithms, surgeons are able to leverage the advanced technology of endoluminal endoscopy while maintaining the depth perception needed for high-precision surgery. As its input, the robotic surgical system takes in a live monocular video feed, and outputs a corresponding live stereoscopic endoscope video feed that has been estimated from the monocular feed—in effect turning a normal (monocular) video feed into an immersive 3D or stereoscopic video feed. This stereoscopic video feed will then be displayed to the surgeon via a 3D display to provide an immersive experience. Because certain portion of the stereoscopic images forming the stereoscopic video feed include predicted images or are based on predicted depths, the system overlays a confidence shading to those portions based on a level associated with the certainty of the predictions.

According to one embodiment of the present disclosure, a surgical robotic system is disclosed. The surgical robotic system includes an endoscopic camera configured to capture images of a three-dimensional (3D) scene and a video processing device coupled to the endoscopic camera and configured to generate a stereoscopic video of the 3D scene based on the images of the 3D scene. The video processing device is configured to render a first view of the 3D scene from a first vantage point based on an image of the captured images and render a second view of the 3D scene from a second vantage point based on the image. The second view includes at least one white area corresponding to occluded regions not visible in the image. The video processing device is further configured to fill-in the at least one white area in the second view, generate a stereoscopic image based on the first view and the second view, and overlay a confidence shading to the at least one filled-in white area in the stereoscopic image.

In an aspect, the video processing device is configured to fill-in the at least one white area in the second view with predicted plausible scenery generated from a neural network configured to predict plausible scenery.

In an aspect, the video processing device is configured to generate a 3D map of the 3D scene as the endoscope moves to different locations throughout the 3D scene.

In an aspect, the video processing device is configured to fill-in the at least one white area in the second view with portions of previously captured images of the 3D scene having been captured by the endoscope at a different location in the 3D scene based on the 3D map.

In an aspect, a form of the confidence shading is selected based on an amount of time elapsed since the previously captured images have been captured by the endoscope at the different location.

In an aspect, the video processing device is configured to generate the stereoscopic image by running multiple independent algorithms on the image, assess a degree to which each of the multiple independent algorithms agree for each pixel in the image, and overlay the confidence shading to portions of the stereoscopic image based on the degree to which each of the multiple independent algorithms agree.

In an aspect, the surgical robotic system further includes a display device operably coupled to the video processing device and configured to display the generated stereoscopic image with the confidence shading overlay.

According to another embodiment of the present disclosure, a method for processing video data of a three-dimensional (3D) scene is provided. The method includes rendering a first view of the 3D scene from a first vantage point based on an image captured by an endoscope, and rendering a second view of the 3D scene from a second vantage point based on the image. The second view includes at least one white area corresponding to occluded regions not visible in the image. The method further includes filling-in the at least one white area in the second view, generating a stereoscopic image based on the first view and the second view, and overlaying a confidence shading to the at least one filled-in white area in the stereoscopic image.

In an aspect, the method further includes predicting plausible scenery with a neural network and filling-in the at least one white area in the second view with the predicted plausible scenery.

In an aspect, the method further includes generating a 3D map of the 3D scene as the endoscope moves to different locations throughout the 3D scene.

In an aspect, the method further includes filling-in the at least one white area in the second view with portions of previously captured images of the 3D scene having been captured by the endoscope at a different location in the 3D scene based on the 3D map.

In an aspect, the method further includes selecting a form of the confidence shading based on an amount of time elapsed since the previously captured images have been captured by the endoscope at the different location.

In an aspect, the method further includes generating the stereoscopic image by running multiple independent algorithms on the image, assessing a degree to which each of the multiple independent algorithms agree for each pixel in the image, and overlaying the confidence shading to portions of the stereoscopic image based on the degree to which each of the multiple independent algorithms agree.

In an aspect, the method further includes displaying the generated stereoscopic image with the confidence shading overlay on a display.

According to another embodiment of the present disclosure, a video processing device of a surgical robotic system is provided. The video processing device is configured to receive images of a three-dimensional (3D) scene captured by an endoscope, render a first view of the 3D scene from a first vantage point based on an image of the received images, and render a second view of the 3D scene from a second vantage point based on the image. The second view includes at least one white area corresponding to occluded regions not visible in the image. The video processing device is further configured to fill-in the at least one white area in the second view, generate a stereoscopic image based on the first view and the second view, and overlay a confidence shading to the at least one filled-in white area in the stereoscopic image.

In an aspect, the video processing device is further configured to fill-in the at least one white area in the second view with predicted plausible scenery generated from a neural network configured to predict plausible scenery.

In an aspect, the video processing device is further configured to generate a 3D map of the 3D scene as the endoscope moves to different locations throughout the 3D scene.

In an aspect, the video processing device is further configured to fill-in the at least one white area in the second view with portions of previously captured images of the 3D scene having been captured by the endoscope at a different location in the 3D scene based on the 3D map.

In an aspect, a form of the confidence shading is selected based on an amount of time elapsed since the previously captured images have been captured by the endoscope at the different location.

In an aspect, the video processing device is further configured to generate the stereoscopic image by running multiple independent algorithms on the image, assess a degree to which each of the multiple independent algorithms agree for each pixel in the image, and overlay the confidence shading to portions of the stereoscopic image based on the degree to which each of the multiple independent algorithms agree.

BRIEF DESCRIPTION OF THE DRAWINGS

Various embodiments of the present disclosure are described herein with reference to the drawings wherein.

4

Figure 1:
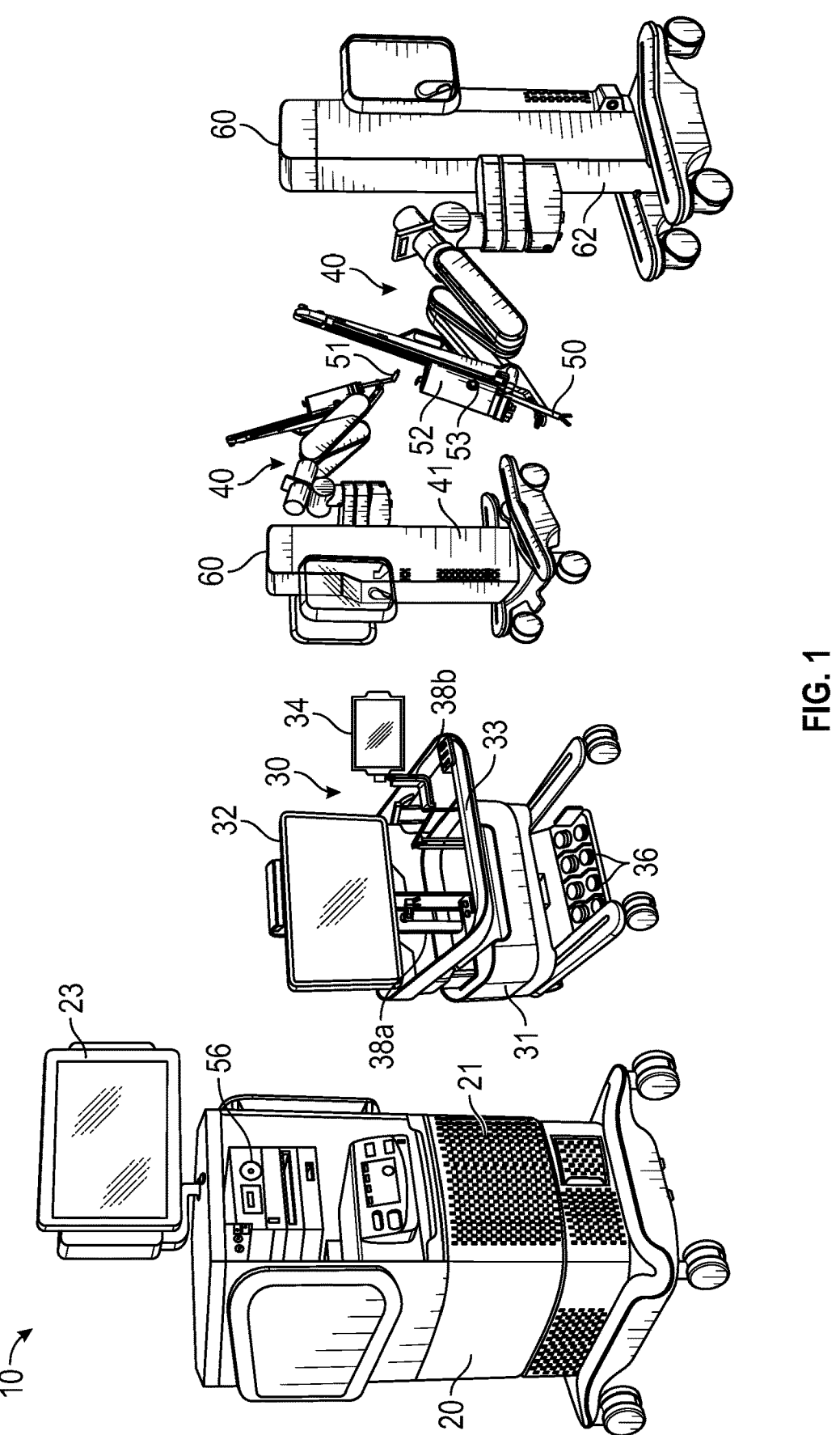
FIG. 1 is a schematic illustration of a surgical robotic system including a control tower, a console, and one or more surgical robotic arms according to an embodiment of the present disclosure.
Figure 2:
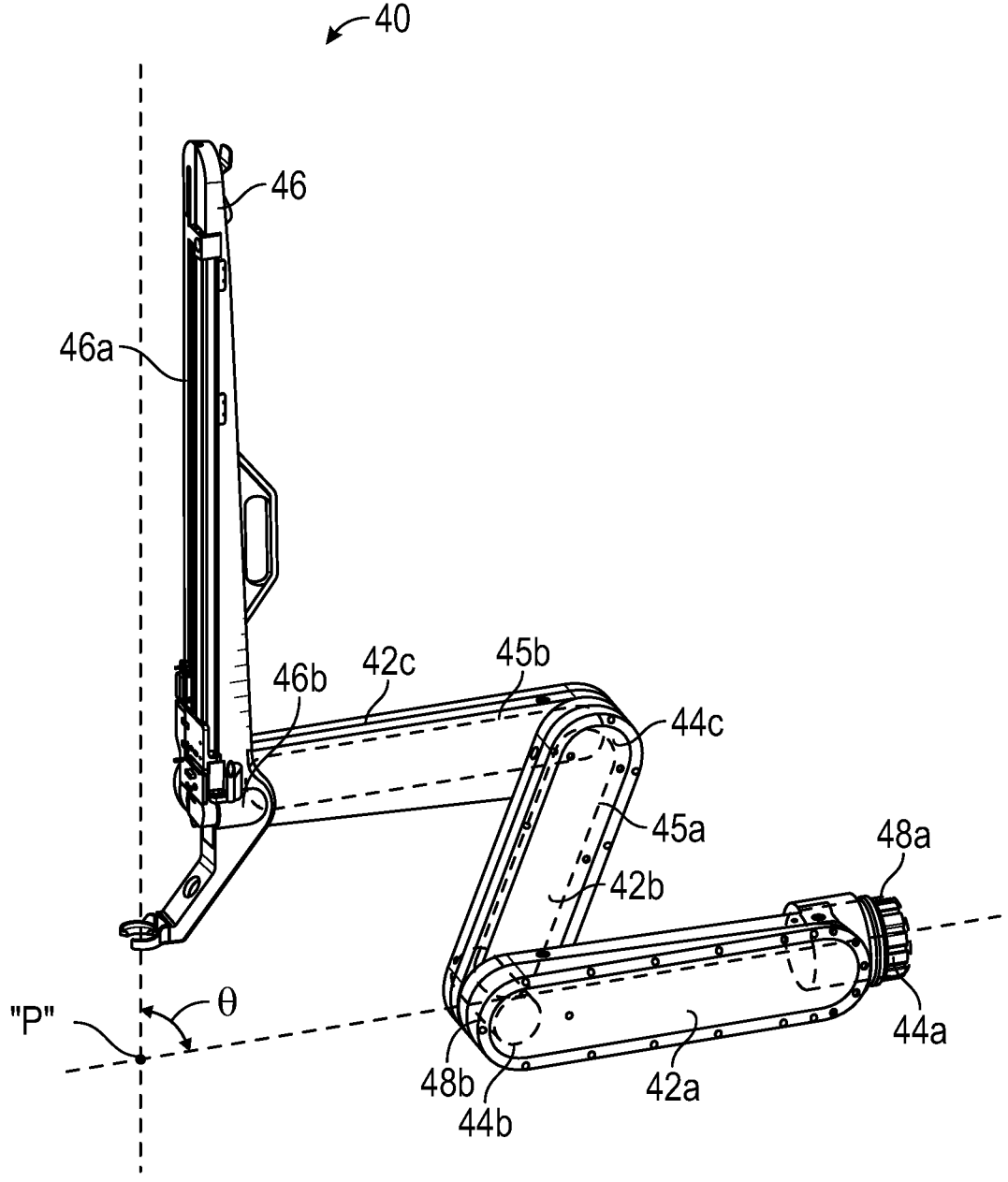
Figure 3:
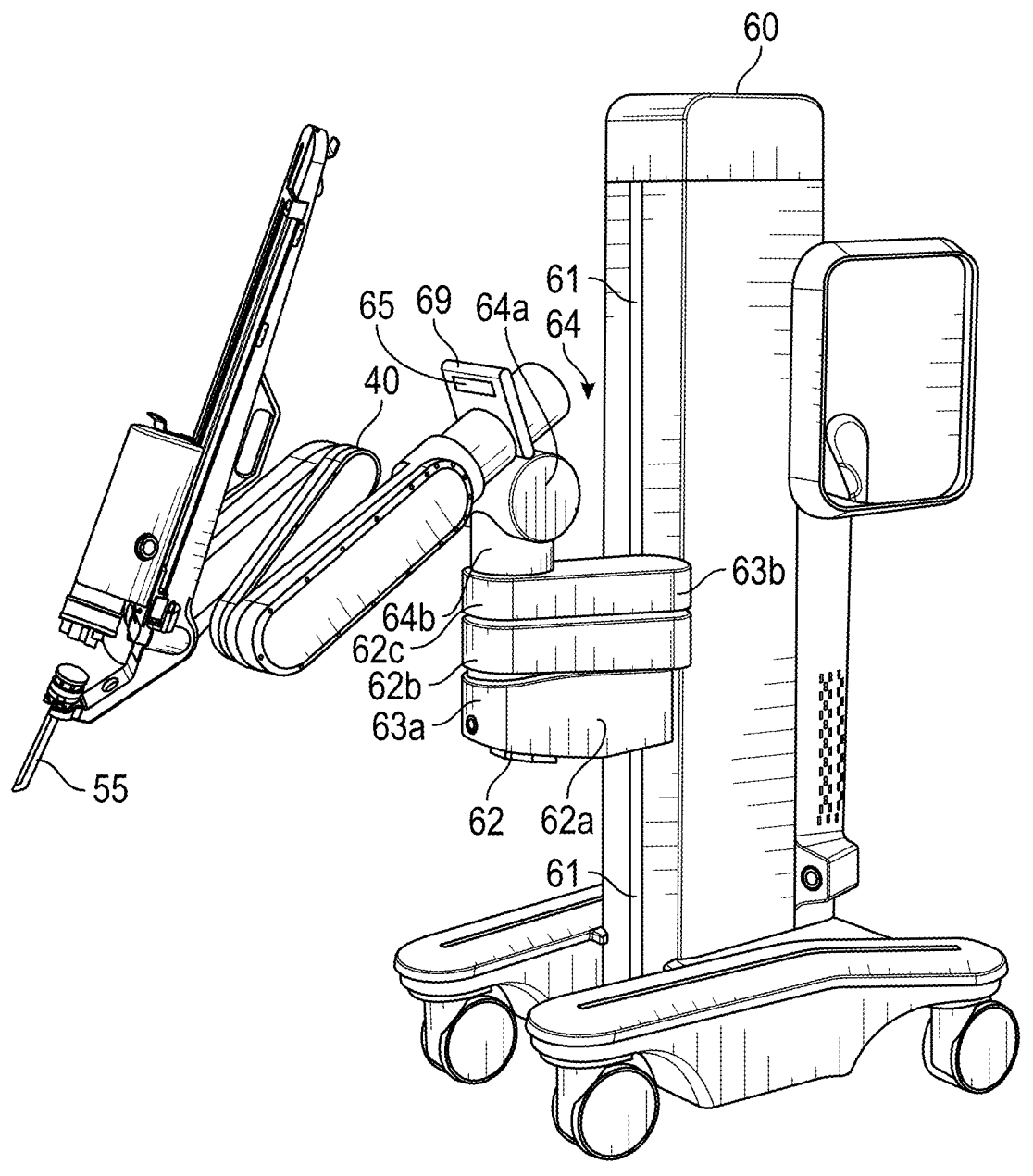
Figure 4:
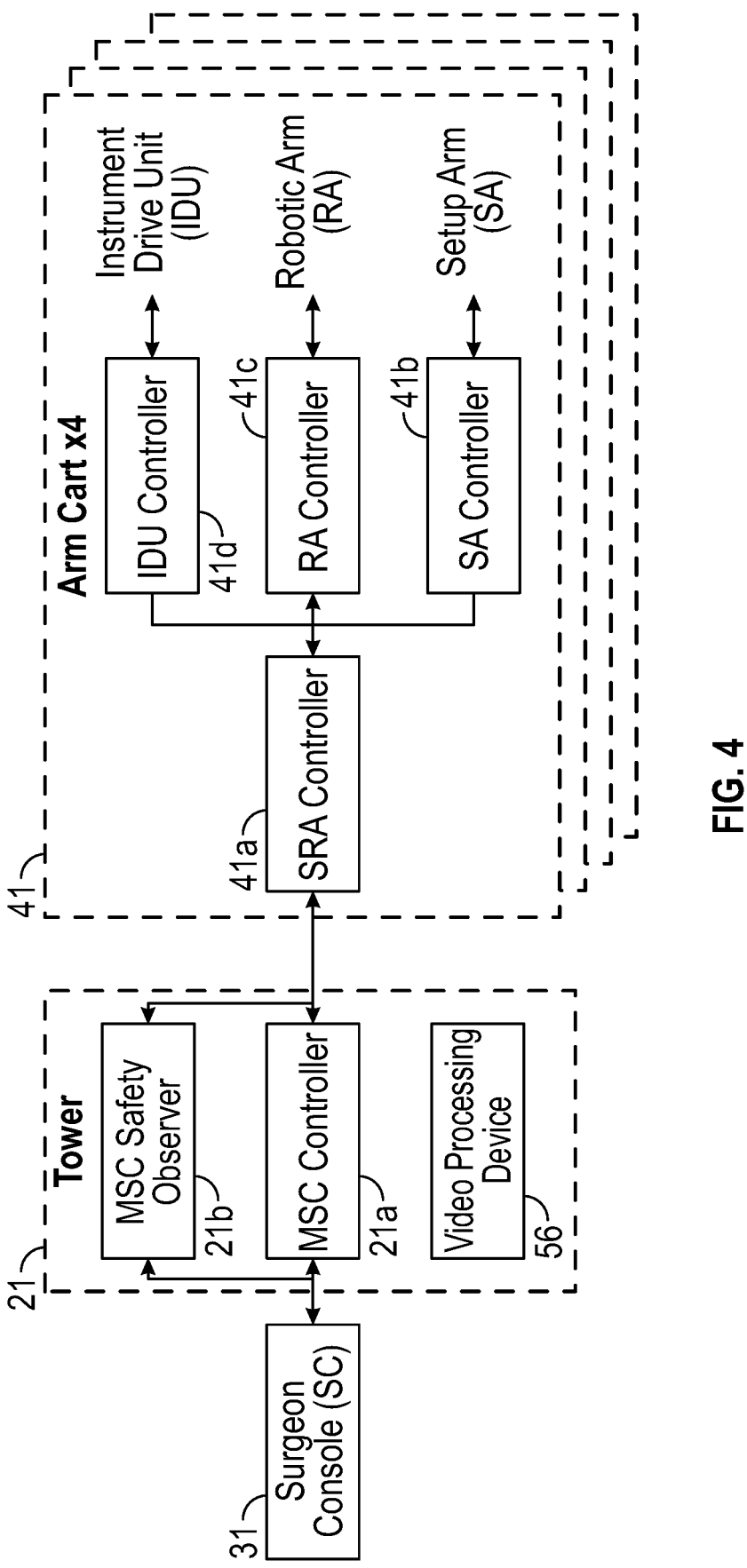
Figure 5:
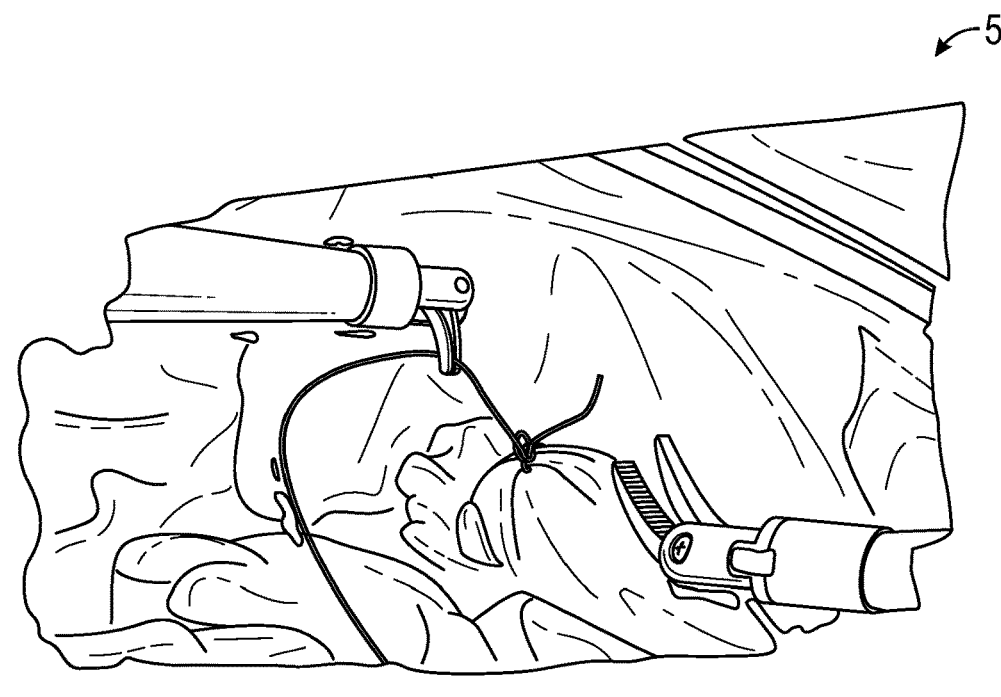
Figure 6:
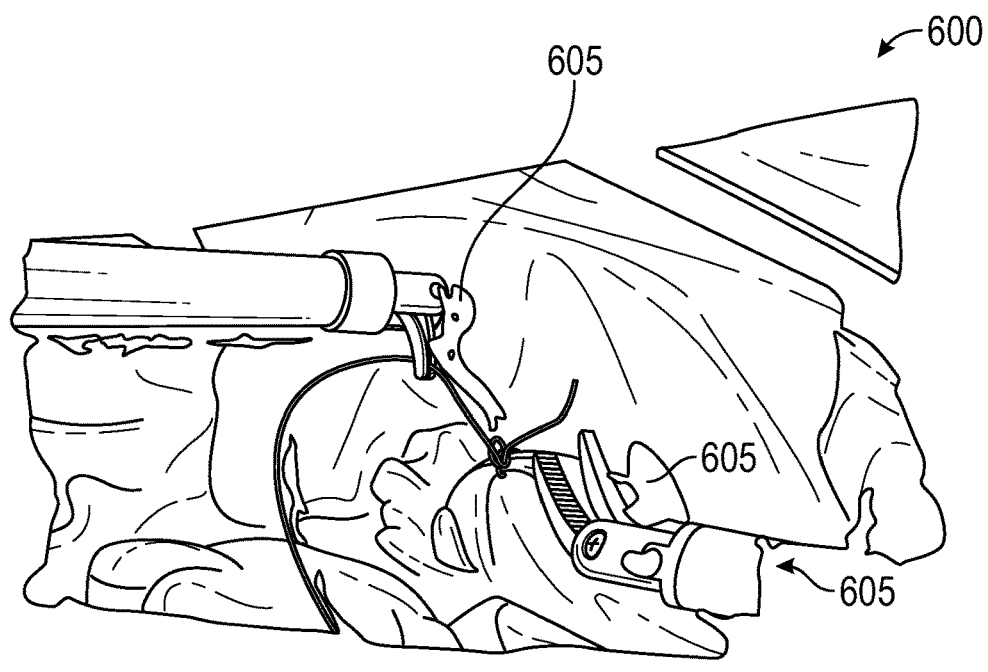
Figure 7:
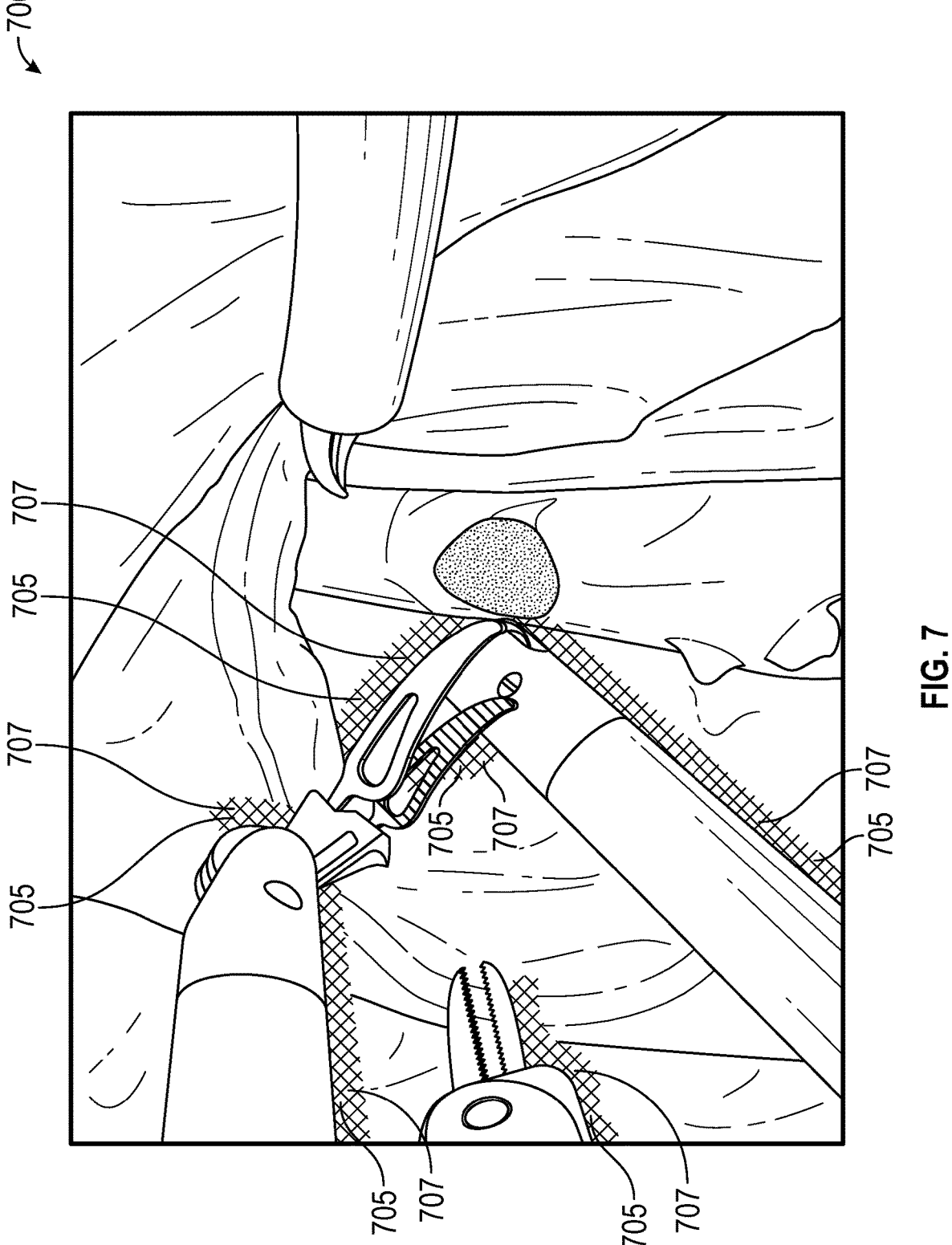

FIG. 2 is a perspective view of a surgical robotic arm of the surgical robotic system of FIG. 1 according to an embodiment of the present disclosure;

FIG. 3 is a perspective view of a setup arm with the surgical robotic arm of the surgical robotic system of FIG. 1 according to an embodiment of the present disclosure;

FIG. 4 is a schematic diagram of a computer architecture of the surgical robotic system of FIG. 1 according to an embodiment of the present disclosure;

FIG. 5 is a view of a 3D scene from a monocular endoscope for display to a left eye;

FIG. 6 is a view of the 3D scene from the monocular endoscope, re-rendered from a shifted vantage point, for display to a right eye;

FIG. 7 is a view of a 3D scene with confidence shading; and

Figure 8:
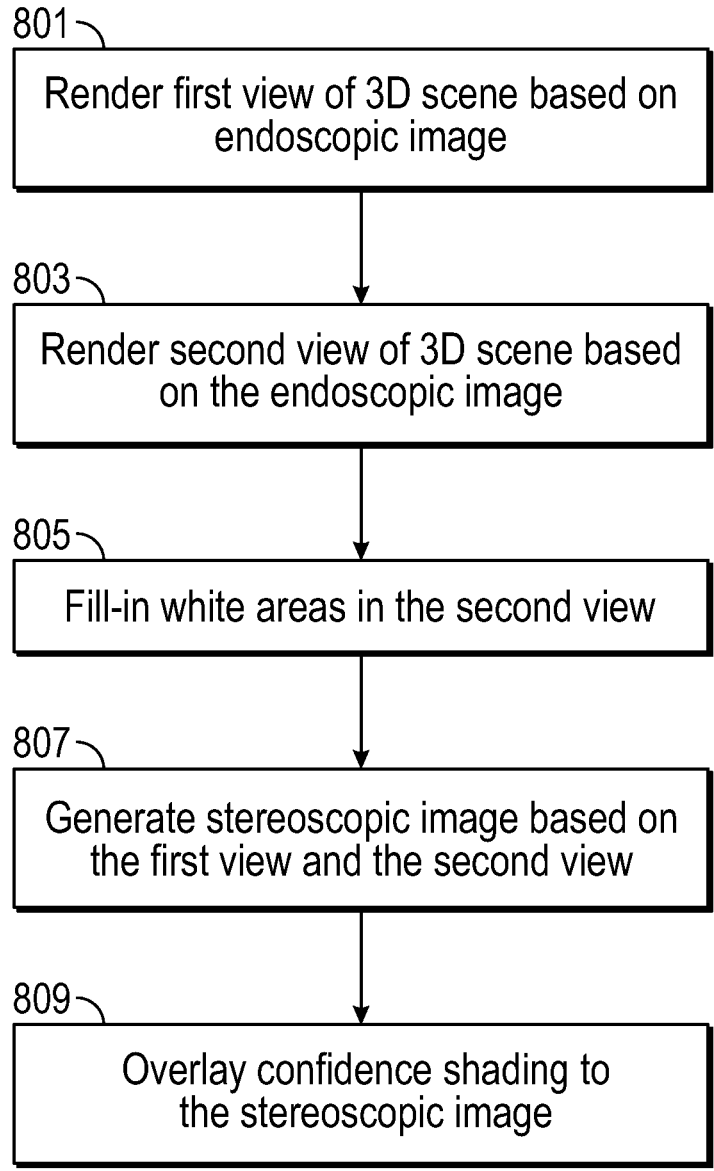

FIG. 8 is a flow chart illustrating a method for generating a stereoscopic video feed with confidence shading.

DETAILED DESCRIPTION

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, a personal computer, or a server system.

As will be described in detail below, the present disclosure is directed to a surgical robotic system, which includes a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscopic camera 51, configured to provide a video feed for the user. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue.

One of the robotic arms 40 may include the endoscopic camera 51 configured to capture video of the surgical site. The endoscopic camera 51 may be a monoscopic endoscope configured to capture images of a 3D scene of the surgical site to produce a video stream of the surgical scene. The endoscopic camera 51 is coupled to a video processing device 56 (FIG. 4), which may be disposed within the control tower 20. The video processing device 56 may be any computing device as described below configured to receive the video feed from the endoscopic camera 51 perform the image processing based on the depth estimating algorithms of the present disclosure and output the processed stereoscopic video stream.

The surgical console 30 includes a first display 32, which displays a video feed of the surgical site provided by camera 51 of the surgical instrument 50 disposed on the robotic arms 40, and a second display 34, which displays a user interface for controlling the surgical robotic system 10. The first and second displays 32 and 34 are touchscreens allowing for displaying various graphical user inputs.

The surgical console 30 also includes a plurality of user interface devices, such as foot pedals 36 and a pair of handle controllers 38a and 38b which are used by a user to remotely control robotic arms 40. The surgical console further includes an armrest 33 used to support clinician's arms while operating the handle controllers 38a and 38b.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38a and 38b.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

With reference to FIG. 2, each of the robotic arms 40 may include a plurality of links 42a, 42b, 42c, which are interconnected at joints 44a, 44b, 44c, respectively. The joint 44a is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62a and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

The actuator 48b of the joint 44b is coupled to the joint 44c via the belt 45a, and the joint 44c is in turn coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

With reference to FIG. 2, the robotic arm 40 also includes a holder 46 defining a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector) of the surgical instrument 50. The holder 46 includes a sliding mechanism 46a, which is configured to move the IDU 52 along the second longitudinal axis defined by the holder 46. The holder 46 also includes a joint 46b, which rotates the holder 46 relative to the link 42c. During endoscopic procedures, the instrument 50 may be inserted through an endoscopic port 55 (FIG. 3) held by the holder 46.

The robotic arm 40 also includes a plurality of manual override buttons 53 (FIGS. 1 and 5) disposed on the IDU 52 and the setup arm 62, which may be used in a manual mode. The user may press one or more of the buttons 53 to move the component associated with the button 53.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgical console 30 about the current position and/or orientation of the handle controllers 38a and 38b and the state of the foot pedals 36 and other buttons. The controller 21a processes these input positions to determine desired drive commands for each joint of the robotic arm 40 and/or the IDU 52 and communicates these to the computer 41 of the robotic arm 40. The controller 21a also receives the actual joint angles measured by encoders of the actuators 48a and 48b and uses this information to determine force feedback commands that are transmitted back to the computer 31 of the surgical console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the IDU 52. The main cart controller 41a also communicates actual joint angles back to the controller 21a.

The setup arm controller 41b controls each of joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the IDU 52. The IDU controller 41d calculates actual angles based on the motor positions and transmits the actual angles back to the main cart controller 41a.

The robotic arm 40 is controlled in response to a pose of the handle controller controlling the robotic arm 40, e.g., the handle controller 38a, which is transformed into a desired pose of the robotic arm 40 through a hand eye transform function executed by the controller 21a. The hand eye function, as well as other functions described herein, is/are embodied in software executable by the controller 21a or any other suitable controller described herein. The pose of one of the handle controller 38a may be embodied as a coordinate position and role-pitch-yaw ("RPY") orientation relative to a coordinate reference frame, which is fixed to the surgical console 30. The desired pose of the instrument 50 is relative to a fixed frame on the robotic arm 40. The pose of the handle controller 38a is then scaled by a scaling function executed by the controller 21a. In embodiments, the coordinate position is scaled down and the orientation is scaled up by the scaling function. In addition, the controller 21a also executes a clutching function, which disengages the handle controller 38a from the robotic arm 40. In particular, the controller 21a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the controller 21a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

In minimally invasive surgeries, the camera 51 may be limited to a monocular camera providing a monocular video feed to the video processing device 56 of the control tower 20. Referring to FIGS. 5-8, the monocular video feed produces a series of images of the 3D scene and transmits the feed to the video processing device 56. With reference to FIG. 8 specifically, in step 801, the video processing device 56 receives the video feed from the endoscopic camera 51 and renders a first view of the 3D scene as image 500 (FIG. 5) which may be used for display to the surgeon's left eye. In step 803, the same image used to render image 500 is also utilized to render a second image 600 (FIG. 6) of the 3D scene from a different perspective. As shown in FIG. 6, the second image 600 includes white areas 605 which are occluded areas of the 3D scene not visible by the endoscope 51 as currently positioned. In step 805, the video processing device 56 fills-in the white areas 605 in the second image 600 with predicted images 705, as described in greater detail below. In step 807, the video processing device 56 generates a stereoscopic image 700 of the 3D scene based on the first image 500 and the second image 600 (with the white areas 605 being filled-in with predicted images 705). A certain level of confidence is associated with the predicted images 705 used to fill-in the white areas 605, which may be useful for the surgeon to be aware of when viewing the generated stereoscopic image 700. Thus, in step 809, the video processing device 56 overlays a confidence shading 707 to the predicted images 705 filling-in the white areas 605 in the stereoscopic image 700. The generated stereoscopic image 700 may then be displayed on the display 32 of the surgical console 30 with the overlayed confidence shading 707.

Steps 801, 803, 805, and 807 may be carried out by the video processing device 56 via various techniques to generate the stereoscopic image 700. In accordance with one aspect of the disclosure, a neural network operates on an input from the monocular video feed of the camera 51, and outputs the data necessary for constructing a stereoscopic video feed to be delivered to the surgical console 30. There are many different representations and output formats possible for this neural network. In one aspect, a left image 500 (FIG. 5) and a right image 600 (FIG. 6) are directly output, leveraging "image-to-image" translation techniques commonly used with convolution neural networks.

In another aspect, a depth map is output, which includes the mapping of each pixel in the input image to a corresponding depth (or distance) from the camera. A second post-processing algorithm or neural network could then use this distance map to reconstruct a 3D point cloud and re-render the image from a slightly shifted viewpoint, thereby simulating an image captured by a second camera (e.g., image 600). An algorithm or neural network could fill-in the white areas 605 in the point cloud with plausible data that were not visible in the monocular video feed, or by using a generative adversarial network variation.

Use of an autoencoder, or other neural network architecture may also allow such white areas 605 to be filled-in. Such white areas 605 could also be filled-in using data from previously observed vantage points during the surgery via SLAM (simultaneous localization and mapping), and by leveraging geometric information from deformable tissue physics models.

Another aspect utilizes a "distortion map," that maps each pixel of the monocular image to and from a perturbed location in a channel of the output image, thus allowing the output image to be constructed directly using this mapping.

In order to ensure consistency across successive video frames, a "smoothing" technique may be used to prevent flickering. Prior techniques from recurrent neural networks (such as Long Short-Term Memory (LSTM)) may be utilized to prevent flickering.

There are many ways that such a neural network could be trained and data obtained. One approach, according to the disclosure, utilizes an existing stereoscopic endoscope and record data from patient procedures. The training task predicts, for example, the right channel image from the left channel video feed. Another approach, according to the disclosure, leverages structure-from-motion (SfM) or simultaneous localization and mapping (SLAM) algorithms to infer depth maps from moving, monocular video sequences and uses the inferred depth maps as training data. According to the disclosure, it is also possible to train the neural network partly on simulated or augmented data, by leveraging a photorealistic 3D surgical simulator in which depth information may be obtained as ground-truth data. Another approach, according to the disclosure, infers ground truth data, that is data collected at scale from real-world scenarios, for in vivo datasets using 3D measurement techniques such as CT scans. Finally, according to the disclosure, ground-truth robotic kinematics information may be used to aid the training process by honing SfM and/or SLAM.

During the training process, a suitable loss function must be used to ensure that the neural network converges to the desired behavior. In accordance with the disclosure, a variety of different loss functions may be used, depending on the architecture of the neural network. In the case where stereoscopic data is present in the training set, the loss function may compute a pixel-wise difference or a disparity between the estimated image (e.g., image 600) and the actual observed image (e.g., image 500). Other techniques from computer vision may also be used to calculate a loss between the generated image and actual image, such as calculating loss at only a subset region (e.g., chosen via SIFT (scale-invariant feature transform) or other robust feature detectors) or by leveraging other features from an "intrinsic image" (e.g., a low-level characteristic of an original image extracted from the original image) estimation. Furthermore, the loss function may take in a variety of inputs, such as a linear combination of the disparity map, the disparity map gradient, and/or the image intensity during training.

If 3D CT scans are used as training data, the depth maps may be converted to point clouds and compared with the ground truth data by attempting to match similar points or by using a volumetric difference error. Other loss functions that combine image camera optics, depth accuracy, minimal distortion, smoothness or consistency across frames, and photorealism (e.g., using a generative adversarial network (GAN)) may also be used.

Another technique, according to the disclosure, involves predicting certain surface features from the monocular endoscope image-such as curvature-instead of using a depth map, and integrating that curvature to obtain a 3D surface model. This 3D surface model may then be re-rendered from a slightly shifted vantage point to produce the second optical channel (e.g., image 600) in real-time.

According to another aspect of the disclosure, the surgical robotic system 10 is capable of allowing for the surgeon to dynamically adjust the "stereo separation distance" of the predicted stereoscopic endoscope video. For example, by turning a knob (not shown) of the surgical robotic system 10 (e.g., a knob of the surgical console 30), a depth scale of the image, or the amount of 3D effect that will be visible to the surgeon may be adjusted.

In accordance with yet another aspect of the disclosure, in order to increase accuracy or "confidence" of the stereoscopic video feed, an SfM or SLAM algorithm may be executed online (e.g., in the cloud or at a remote processing location), in parallel with the neural network, when a live surgery is taking place. The SfM will generate a coarse point cloud 3D reconstruction of the endoscope feed as the endoscope 51 moves, which can be used to dynamically adjust the scale and/or accuracy of the stereo video feed in real-time in order to improve the accuracy of the system and/or the 3D reconstruction. A SLAM algorithm could also be used to fill-in textures or holes for points that are not visible currently from the vantage point of the monocular video feed, but were visible earlier from a different vantage point. Finally, the surgeon may "pause", and virtually pan around the 3D construction view, without physically moving the endoscope 51.

According to one embodiment, the video processing device 56 is configured to execute two image processing algorithms, namely an analytical reconstruction algorithm and a deep learning algorithm. In particular, the video processing device 56 uses an analytical reconstruction algorithm as a cross-check/validation of the deep learning algorithm. Both algorithms run in real time, processing the same endoscope images. The deep learning algorithm produces a dense depth map, and the analytical reconstruction algorithm may produce only a sparse dense map for a subset of points in the image. The video processing device 56 then compares the corresponding depth values (dense versus deep learning) to see how closely they agree. If their difference exceeds a tolerance (either absolute or as a percentage) over a large fraction of key areas in the image, then the generated depth map may be deemed unreliable and unsuitable for use in certain applications (such as automated suturing). In this way, the video processing device 56 may use two (or even more) independent implementations of depth mapping algorithms to check how well, or to calculate a degree to which, they agree with each other.

The video processing device 56, rather than validate the output of the deep learning algorithm, utilizes the data from the analytical reconstruction algorithm to correct the deep learning algorithm in real-time. If the deep learning and analytical reconstruction algorithm produce disagreeing depth estimates for certain key points, the dense deep learning algorithm output can be locally scaled, averaged, or spatially warped by adjusting its parameters to better match the analytical reconstruction algorithm, which may be more reliable for those key points. It may also be possible to incorporate "correction inputs" into the deep learning network itself to accommodate some of these corrections.

Other algorithms may be used to check depth map plausibility, to rule out strange or unexpected depth maps. A neural network may be trained review generated depth maps and reject faulty ones, thus acting as another layer of verification. Other simpler algorithms may also be used to detect sudden unexpected depth jumps in tissue-like regions that are expected to be smooth. Such algorithms could identify regions of anomalous depth maps to assess reliability.

The video processing device 56 may receive physical parameter data from the instrument 50, and the robotic arm 40 holding the instrument 50. In particular, robotic "touch" (e.g., recorded as environmental torque by torque sensors of the robotic arm 40), may be used to refine or validate the depth map. The robotic arm 40 is calibrated to a known hand-eye matrix (e.g., the relationship between the 3D position of the robotic arm 40 and where the instrument 50 held by the robotic arm 40 appears on the screen is known). Thus, when instrument 50 is touching or grasping tissue or another object in the surgical scene, this contact is inferred via force or torque sensors. Touch may also be determined visually based on deformation of the tissue. Touch implies that the depth of the instrument tip is approximately equal to the depth of the surgical scene, allowing the position of the instrument 50, which is known from the robotic arm 40 torque sensors to be used as a proxy for depth in that location. These position estimates can be used as a cross-check or refinement for the optically-estimated depth.

The generated depth map may be combined with other 3D data such as various imaging scans (e.g., CAT scans, MRI, ultrasound, etc.). Such 3D data may be overlayed over the depth map and may be used to identify critical structures. The depth map may then be used by the computer 21 to generate virtual walls around critical structures, which would prevent movement of the instrument 50 beyond the virtual walls, thus limiting operating space of the robotic arms 40.

When predicting a stereoscopic image (3D image) from a 2D image, there will inherently be white areas 605 (e.g., portions of the image for which it is not possible to see because those portions of the image are obscured). This poses two problems: 1) realistically filling-in the white areas 605 with plausible imagery; and 2) ensuring that the filling-in of obscured regions with plausible imagery is not misleading to the surgeon and compromising to safety by displaying incorrect information.

As described above, neural network architectures and the like may be used to fill-in the white areas 605 with predicted images 705. Regardless of how the filling-in is performed, and how the predicted images 705 are generated, since the predicted images 705 are ultimately images generated for areas that are not visible, a level of confidence is associated with the predicted images 705. With respect to step 809 of FIG. 8, one aspect of this disclosure relates to how "confidence" of the filled-in white areas 605 are displayed on the stereoscopic image 700 to the surgeon. Since converting a monocular endoscope feed to a stereoscopic feed is an inherently under-constrained problem, that is a system of polynomial equations which has fewer equations than unknowns, the neural network will at times predict plausible stereoscopic data that may not completely match reality. Other times (such as predicting in the face of smoke, obstructions, or around areas that have not yet been observed), the neural network will effectively be predicting unseen structure during surgery. These filled-in areas will be of relatively lower "confidence" as compared to other areas that were filled-in with images previously seen by the endoscope 51. As illustrated in FIG. 7, the surgical robotic system 10 may visually display a measure of "confidence" as confidence shading 707 in these predictions, either by changing color, texture, pixelization, resolution, or by other visual means. Related to this, certain features of surgery (such as cautery tool energy activation) may be disabled generally, or in regions where the confidence level is below a threshold, until the "confidence" reaches a certain predetermined or desired threshold.

With reference to FIGS. 5 and 6, there will be regions of the surgical scene that will be out of view of the single monocular camera, but that will be shown to the surgeon via the second view (FIG. 6) of the stereoscopic display. FIGS. 5 and 6 illustrate two views of the same 3D scene, rendered from slightly different vantage points. FIG. 5 illustrates the view from the monocular endoscope displayed to the left eye-note that there are ideally no occluded/white "unknown" areas. FIG. 6 illustrates the same 3D scene, re-rendered from a shifted vantage point to the right for display to the surgeon's right eye. In FIG. 6, white areas 605 exist in obstructed areas (e.g., behind tools and anatomy), which represent areas that cannot be seen from the monocular image, but would need to be displayed to surgeon in the right eye when generating stereoscopy. Those white areas 605 are areas that are of low confidence where imagery would be "guessed" and filled-in with a predicted image 705.

Algorithmically, identifying the region for confidence shading 707 (e.g., the occluded regions) may be accomplished by traditional computer vision techniques by detecting the white areas 605 in the rendering of image 600. More specifically, for each pixel, the 3D rendering algorithm used to produce the image may determine whether or not 3D content appears at the pixel, and hence mark that pixel as an occluded area for which confidence shading 707 should be applied. Equivalently, a virtual ray may be cast for each pixel in the rendered image and a determination may be made as to whether the virtual ray intersects any scenery; if not, then that pixel is occluded. With a purely disparity-based or warping-based approach, a similar technique may be used to see whether any portion of the source image was overlaid on the target image at that pixel. In one aspect, the confidence shading 707 may be "leaked" or grown from the right eye display (e.g., image 600) to the left eye display (e.g., image 500) to produce a more 3D effect.

Algorithmically, the form or the nature of the confidence shading 707 may be selected based on the amount or degree of uncertainty. If the SLAM/SfM approach is utilized to conduct the hole-filling described above, then the occluded regions (e.g., white areas 605) will be filled-in with imagery as it was previously seen by the endoscope when the endoscope was at a different location or orientation. If that imagery was seen very recently (e.g., before a period of time of three seconds elapsed), then the video processing device 56 determines that the occluded area is the same as it was last observed, leading to a high degree of confidence that the predicted images 705 used to fill-in the white areas 605 match the actual appearance of the occluded area. In such a case, no confidence shading 707 or a low degree of shading may be used to convey uncertainty, since the predicted images 705 are likely to be accurate. However, if the occluded area was seen after a long period of time elapsed (e.g., more than three minutes ago), then the video processing device 56 determines that the occluded area is not the same as it has been last observed leading to a lower degree of confidence since something might have changed since it was last observed. In such a case, the confidence shading 707 may be displayed more visibly or in another more pronounced form. In this sense, the nature or form of the confidence shading 707 (e.g., its transparency or other aspects of its appearance) could be modified based on the amount of time elapsed since the occluded region was last observed. For occluded areas that have never been seen at all during the procedure (and for which a GAN if used, for example, to predict scenery), the confidence shading 707 could relatedly be more pronounced to indicate that there is high degree of uncertainty associated with the predicted images 705 utilized to fill-in the white areas 605.

Similar to the aspect of using "time last seen" as a heuristic for determining a level of confidence associated with the predicted images 705 (and how opaque or the selected form of the confidence shading 707), other surgical-specific heuristics can similarly be used. For example, if the video processing device 56 determines that the surgical scene is likely to have changed (for reasons other than the amount of time that has elapsed since the occluded region has been observed), the video processing device 56 may indicate a higher level of uncertainty represented in the confidence shading 707. For example, if tissue is being moved/manipulated or dissected, or if electrosurgical tools are active that could cause changes in color or shape, etc., the video processing device 56 may determine that it is less likely that the occluded area is the same as previously observed, and therefore select the appropriate confidence shading 707 based on the determined low degree of confidence.

Separate from the issue of occluded areas described above, another distinct way in which uncertainty (e.g., a lower degree of confidence) can arise is in the 3D depth/disparity calculations themselves (which are used to produce the 3D effect in the stereoscopic image 700). As described above, creating a 3D scene from a single 2D image is an inherently underconstrained problem, and any algorithms that produce a sense of depth from a single monocular frame must, at some level, be "guessing" that depth based on context.

To illustrate this notion of underconstraint, consider two scenarios: (1) an endoscope is looking at a surgical scene, and (2) and endoscope is looking at a flat photograph of the same surgical scene. A monocular camera will not be able to tell the difference between those two; each pixel will be identical in both (1) and (2). Hence, an algorithm that transforms the single monocular frame into a stereoscopic/3D version will incorrectly produce the same 3D scenery for both—despite the fact that the photograph is flat, and has no depth. True stereoscopy would be able to infer that the photograph is flat. This example, though somewhat contrived, illustrates the underconstrained nature of depth calculations for a single frame. Thus, there will be uncertainty and a lower degree of confidence in the true depth since it cannot be uniquely determined without additional information. The video processing device 56 is configured to select the form or nature of the confidence shading 707 based on this source of uncertainty in the depth calculations themselves. Algorithmically, there are several ways to achieve this selection, described in turn below:

In one embodiment, a neural network may output per-pixel confidence. In particular, a neural network may be trained to predict a confidence value (or an inferred estimated standard deviation in the depth value) at each pixel, along with the actual depth/disparity output may be utilized. Areas of low confidence could be conveyed to the surgeon through the confidence shading 707. The training of the neural network may be accomplished by assessing the accuracy of depth estimates based on ground-truth measured depth data, and highlighting areas where there is a large discrepancy between predicted and measured values.

In another embodiment multiple independent algorithms are run simultaneously and the degree to which they agree is assessed to determine the level of confidence. As described above, in one aspect, multiple neural networks (with different architectures, different sets of training data, different parameters, etc.) could be run in parallel, each taking as input the same monocular image frame and estimating depth to produce stereoscopy. Pixels where the networks output similar values suggest that there is high level of confidence there since the different networks agree and therefore little to no confidence shading 707 is applied to these areas. On the other hand, pixels where the networks output significantly different values suggest a lower level of confidence and should have relatively more confidence shading 707 applied.

In another aspect, the output of SLAM or SfM algorithm is compared to determine the level of confidence. In the case when the endoscope is moving significantly and the anatomy is relatively still, depth calculations may be made more accurately by using data across time-hence, getting around the underconstrained limitation of single-frame depth estimation by using multiple frames. If the current depth estimate diverge significantly from a 3D model produced by SLAM or SfM, those areas are shaded as having lower levels of confidence.

Though each of the above three examples are described individually, it is envisioned that some or all approaches may be utilized as heuristics.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical robotic system comprising:
an endoscopic camera configured to capture images of a three-dimensional (3D) scene; a video processing device coupled to the endoscopic camera and configured to generate a stereoscopic video of the 3D scene based on the images of the 3D scene, the video processing device configured to:
render a first view of the 3D scene from a first vantage point based on an image of the captured images;
render a second view of the 3D scene from a second vantage point based on the image, the second view including at least one white area corresponding to occluded regions not visible in the image;
fill-in the at least one white area in the second view;
generate a stereoscopic image based on the first view and the second view; and
overlay a confidence shading to the at least one filled-in white area in the stereoscopic image based on a degree of uncertainty associated with the at least one filled-in white area.

2. The surgical robotic system according to claim 1, wherein the video processing device is configured to fill-in the at least one white area in the second view with predicted plausible scenery generated from a neural network configured to predict plausible scenery.

3. The surgical robotic system according to claim 1, wherein the video processing device is configured to generate a 3D map of the 3D scene as the endoscope moves to different locations throughout the 3D scene.

4. The surgical robotic system according to claim 3, wherein the video processing device is configured to fill-in the at least one white area in the second view with portions of previously captured images of the 3D scene having been captured by the endoscope at a different location in the 3D scene based on the 3D map.

5. The surgical robotic system according to claim 4, wherein a form of the confidence shading is selected based on an amount of time elapsed since the previously captured images have been captured by the endoscope at the different location.

6. The surgical robotic system according to claim 1, wherein the video processing device is configured to:
generate the stereoscopic image by running multiple independent algorithms on the image;
assess a degree to which each of the multiple independent algorithms agree for each pixel in the image; and
overlay the confidence shading to portions of the stereoscopic image based on the degree to which each of the multiple independent algorithms agree.

7. The surgical robotic system according to claim 1, further comprising a display device operably coupled to the video processing device and configured to display the generated stereoscopic image with the confidence shading overlay.

8. A method for processing video data of a three-dimensional (3D) scene, the method comprising:
rendering a first view of the 3D scene from a first vantage point based on an image captured by an endoscope;
rendering a second view of the 3D scene from a second vantage point based on the image, the second view including at least one white area corresponding to occluded regions not visible in the image;
filling-in the at least one white area in the second view;
a stereoscopic image based on the first view and the second view; and
overlaying a confidence shading to the at least one filled-in white area in the stereoscopic image based on a degree of uncertainty associated with the at least one filled-in white area.

9. The method according to claim 8, further comprising:
predicting plausible scenery with a neural network; and
filling-in the at least one white area in the second view with the predicted plausible scenery.

10. The method according to claim 8, further comprising generating a 3D map of the 3D scene as the endoscope moves to different locations throughout the 3D scene.

11. The method according to claim 10, further comprising filling-in the at least one white area in the second view with portions of previously captured images of the 3D scene having been captured by the endoscope at a different location in the 3D scene based on the 3D map.

12. The method according to claim 11, further comprising selecting a form of the confidence shading based on an amount of time elapsed since the previously captured images have been captured by the endoscope at the different location.

13. The method according to claim 8, further comprising:
generating the stereoscopic image by running multiple independent algorithms on the image;
assessing a degree to which each of the multiple independent algorithms agree for each pixel in the image; and overlaying the confidence shading to portions of the stereoscopic image based on the degree to which each of the multiple independent algorithms agree.

14. The method according to claim 8, further comprising displaying the generated stereoscopic image with the confidence shading overlay on a display.

15. A video processing device of a surgical robotic system, the video processing device configured to:

receive images of a three-dimensional (3D) scene captured by an endoscope;

render a first view of the 3D scene from a first vantage point based on an image of the received images;

render a second view of the 3D scene from a second vantage point based on the image, the second view including at least one white area corresponding to occluded regions not visible in the image;

fill-in the at least one white area in the second view;

generate a stereoscopic image based on the first view and the second view; and overlay a confidence shading to the at least one filled-in white area in the stereoscopic image based on a degree of uncertainty associated with the at least one filled-in white area.

16. The video processing device according to claim 15, further configured to fill-in the at least one white area in the second view with predicted plausible scenery generated from a neural network configured to predict plausible scenery.

17. The video processing device according to claim 15, further configured to generate a 3D map of the 3D scene as the endoscope moves to different locations throughout the 3D scene.

18. The video processing device according to claim 17, further configured to fill-in the at least one white area in the second view with portions of previously captured images of the 3D scene having been captured by the endoscope at a different location in the 3D scene based on the 3D map.

19. The video processing device according to claim 15, wherein a form of the confidence shading is selected based on an amount of time elapsed since the previously captured images have been captured by the endoscope at the different location.

20. The video processing device according to claim 15, further configured to:

generate the stereoscopic image by running multiple independent algorithms on the image;

assess a degree to which each of the multiple independent algorithms agree for each pixel in the image; and overlay the confidence shading to portions of the stereoscopic image based on the degree to which each of the multiple independent algorithms agree.

* * * * *